United States Patent
Debardi et al.

(10) Patent No.: US 8,838,236 B2
(45) Date of Patent: Sep. 16, 2014

(54) WEARABLE CARDIAC DEFIBRILLATOR SYSTEM WITH ANTI-BRADYARRHYTHMIA PACING AND METHODS

(71) Applicant: Physio-Control, Inc., Redmond, WA (US)

(72) Inventors: Gary Debardi, Kirkland, WA (US); Isabelle Banville, Newcastle, WA (US); Ronald Eugene Stickney, Edmonds, WA (US)

(73) Assignee: Physio-Control. Inc., Redmond, WA (US)

( * ) Notice: Subject to any disclaimer, the term of this patent is extended or adjusted under 35 U.S.C. 154(b) by 0 days.

(21) Appl. No.: 14/029,589

(22) Filed: Sep. 17, 2013

(65) Prior Publication Data

US 2014/0088660 A1   Mar. 27, 2014

Related U.S. Application Data

(60) Provisional application No. 61/704,390, filed on Sep. 21, 2012.

(51) Int. Cl.
*A61N 1/00*   (2006.01)
*A61N 1/39*   (2006.01)

(52) U.S. Cl.
CPC ............ *A61N 1/3987* (2013.01); *A61N 1/3993* (2013.01)
USPC .................................. 607/7; 607/10; 607/27

(58) Field of Classification Search
CPC ............................ A61N 1/3962; A61N 1/339
USPC .................................................. 607/7, 10, 27
See application file for complete search history.

(56) References Cited

U.S. PATENT DOCUMENTS

| | | | |
|---|---|---|---|
| 6,374,138 | B1 | 4/2002 | Owen et al. |
| 6,427,083 | B1 | 7/2002 | Owen et al. |
| 2007/0049979 | A1 | 3/2007 | Bardy et al. |
| 2011/0046496 | A1* | 2/2011 | Zhang et al. .................. 600/508 |
| 2012/0150244 | A1* | 6/2012 | Freeman et al. .................. 607/3 |
| 2012/0296384 | A1* | 11/2012 | Daynes et al. .................... 607/5 |

* cited by examiner

*Primary Examiner* — Nicole F Lavert
(74) *Attorney, Agent, or Firm* — Kavounas Patent Law Office, PLLC.

(57) ABSTRACT

In one embodiment, a wearable defibrillation system may sense whether its wearer meets an unconscious bradyarrhythmia condition that can be associated with becoming unconscious. Even though such a condition might not be helped with a defibrillation pulse, the wearable defibrillation system may still administer pacing pulses to prevent the bradycardia from becoming worse, such as a sudden cardiac arrest. In some embodiments, the pacing pulses are administered at a frequency too slow for the patient to regain consciousness. An advantage is that, because the patient remains unconscious, he does not experience the sometimes severe discomfort due to the pacing pulses.

30 Claims, 6 Drawing Sheets

WEARABLE DEFIBRILLATOR SYSTEM

FIG. 3A <u>PACING PULSES (MAINTAINING PATIENT UNCONSCIOUS)</u>

FIG. 3B <u>PACING ON-DEMAND PULSES (ALLOWING FOR PERFUSION)</u>

FIG. 3C <u>PACING PULSES (ENSURING PATIENT UNCONSCIOUS)</u>

FIG. 4

FIG. 5   *METHODS*

FIG. 6

WEARABLE CARDIAC DEFIBRILLATOR SYSTEM WITH ANTI-BRADYARRHYTHMIA PACING AND METHODS

CROSS REFERENCE TO RELATED PATENT APPLICATIONS

This patent application claims priority from U.S. Provisional Patent Application Ser. No. 61/704,390, filed on Sep. 21, 2012, titled: "Titrated Transthoracic Pacing System to Temporarily Sustain Life", the disclosure of which is hereby incorporated by reference for all purposes.

BACKGROUND

When people suffer from some types of heart arrhythmia, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. Population at a higher risk includes individuals who have had a heart attack, or a prior SCA episode. People with an increased risk of SCA are recommended to receive an Implantable Cardioverter Defibrillator ("ICD"). An ICD continuously monitors the person's electrocardiogram ("ECG"). If certain types of heart arrhythmia are detected, then the ICD delivers an electric shock through the heart.

Before receiving an ICD, people with an increased risk of an SCA are sometimes given a wearable external defibrillator system. A wearable defibrillator system typically includes a harness, vest, or other garment for wearing by the patient. The system includes a defibrillator and external electrodes, which are attached on the inside of the harness, vest, or other garment. When the patient wears the system, the external electrodes may then make good electrical contact, with the person's skin, and therefore can help monitor the patient's ECG. If a shockable heart arrhythmia is detected, then the defibrillator delivers the appropriate electric shock through the body, and thus through the heart.

BRIEF SUMMARY

The present description gives instances of devices, systems, software, and methods, the use of which may help overcome problems and limitations of the prior art.

In one embodiment, a wearable defibrillation system may sense whether its wearer meets an unconscious bradyarrhythmia condition that can be associated with becoming unconscious. Even though such a condition might not be helped with a defibrillation pulse, the wearable defibrillation system may administer pacing pulses to prevent the bradycardia from becoming worse, such as a sudden cardiac arrest. In some embodiments, the pacing pulses are administered at a frequency too slow for the patient to regain consciousness. An advantage is that, because the patient remains unconscious, he does not experience the sometimes severe discomfort due to the pacing pulses.

These and other features and advantages of this description will become more readily apparent from the following Detailed Description, which proceeds with reference to the drawings, in which:

DETAILED DESCRIPTION

As has been mentioned, the present description is about wearable defibrillation systems, software, and methods. Embodiments are now described in more detail.

A wearable defibrillator system made according to embodiments has a number of components. One of these components is a support structure, which is configured to be worn by the patient. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

Figure 1:
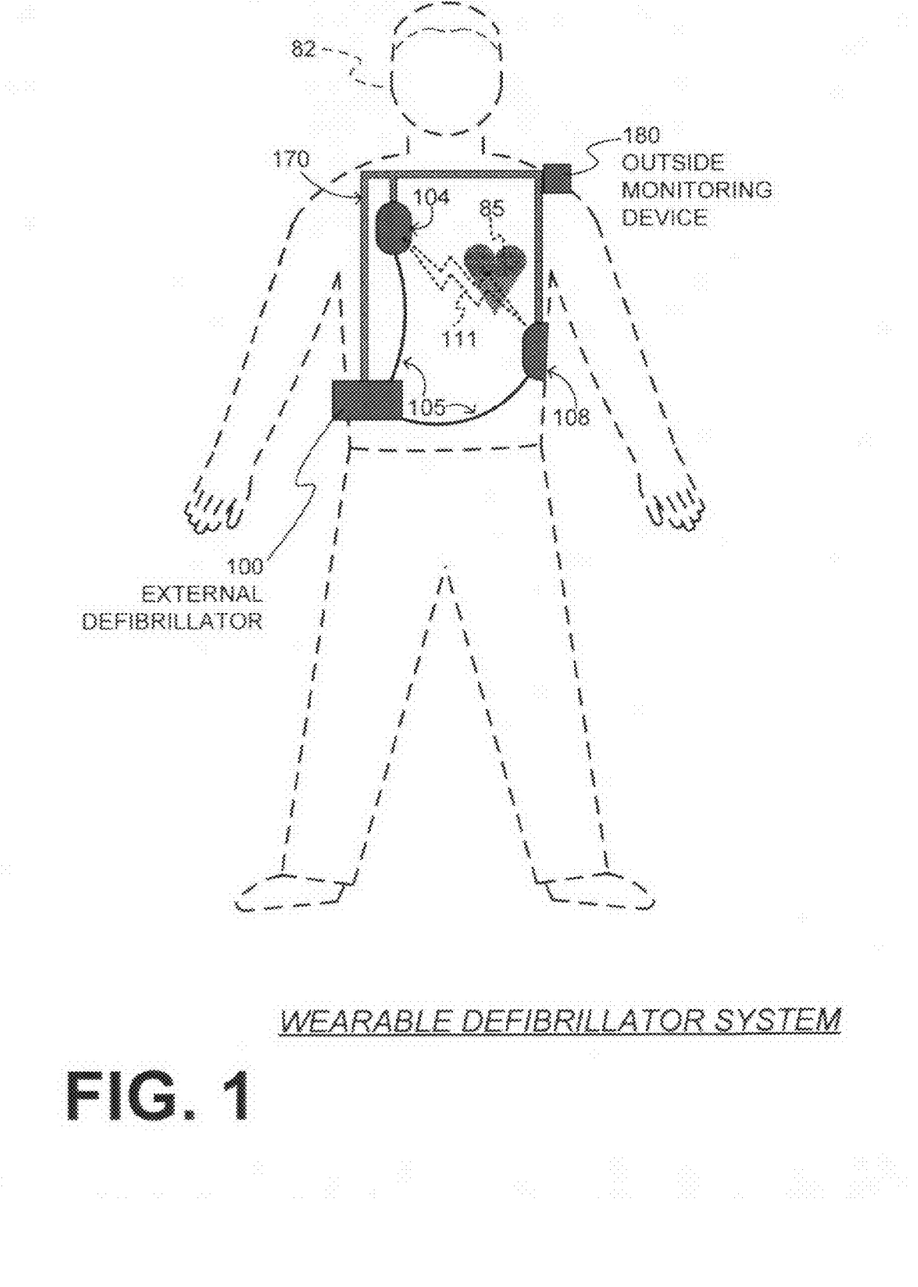
FIG. 1 is a diagram of components of a wearable defibrillator system, made according to embodiments.

FIG. 1 depicts components of a wearable defibrillator system made according to embodiments, as it might be worn by a patient 82. Patient 82 may also be referred to as person 82, and/or wearer 82 since he or she wears components of the wearable defibrillator system.

In FIG. 1, a generic support structure 170 is shown relative to the body of person 82, and thus also relative to his or her heart 85. Structure 170 could be a harness, a vest, one or more belts, a garment, as per the above; it could be implemented in a single component, or multiple components, and so on. Structure 170 is wearable by person 82, but the manner of wearing it is not depicted, as structure 170 is depicted only generally in FIG. 1.

A wearable defibrillator system is configured to defibrillate the patient, by delivering electrical charge to the patient's body in the form of an electric shock or one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, all components of defibrillator 100 can be therefore coupled to support structure 170. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of person 82. Pulse 111 can also be one or more pacing pulses, and so on.

A prior art defibrillator typically decides whether to defibrillate or not based on an electrocardiogram ("ECG") of the patient. However, defibrillator 100 can defibrillate, or not defibrillate, also based on other inputs.

The wearable defibrillator system may optionally include an outside monitoring device 180. Device 180 is called an "outside" device because it is provided as a standalone, for example not within the housing of defibrillator 100. Device 180 is configured to monitor at least one local parameter. A local parameter can be a parameter of patient 82, or a parameter of the wearable defibrillation system, or a parameter of the environment, as will be described later in this document.

Optionally, device 180 is physically coupled to support structure 170. In addition, device 180 can be communicatively coupled with other components, which are coupled to support structure 170. Such a component can be a communication module, as will be deemed applicable by a person skilled in the art in view of this disclosure.

Figure 2:
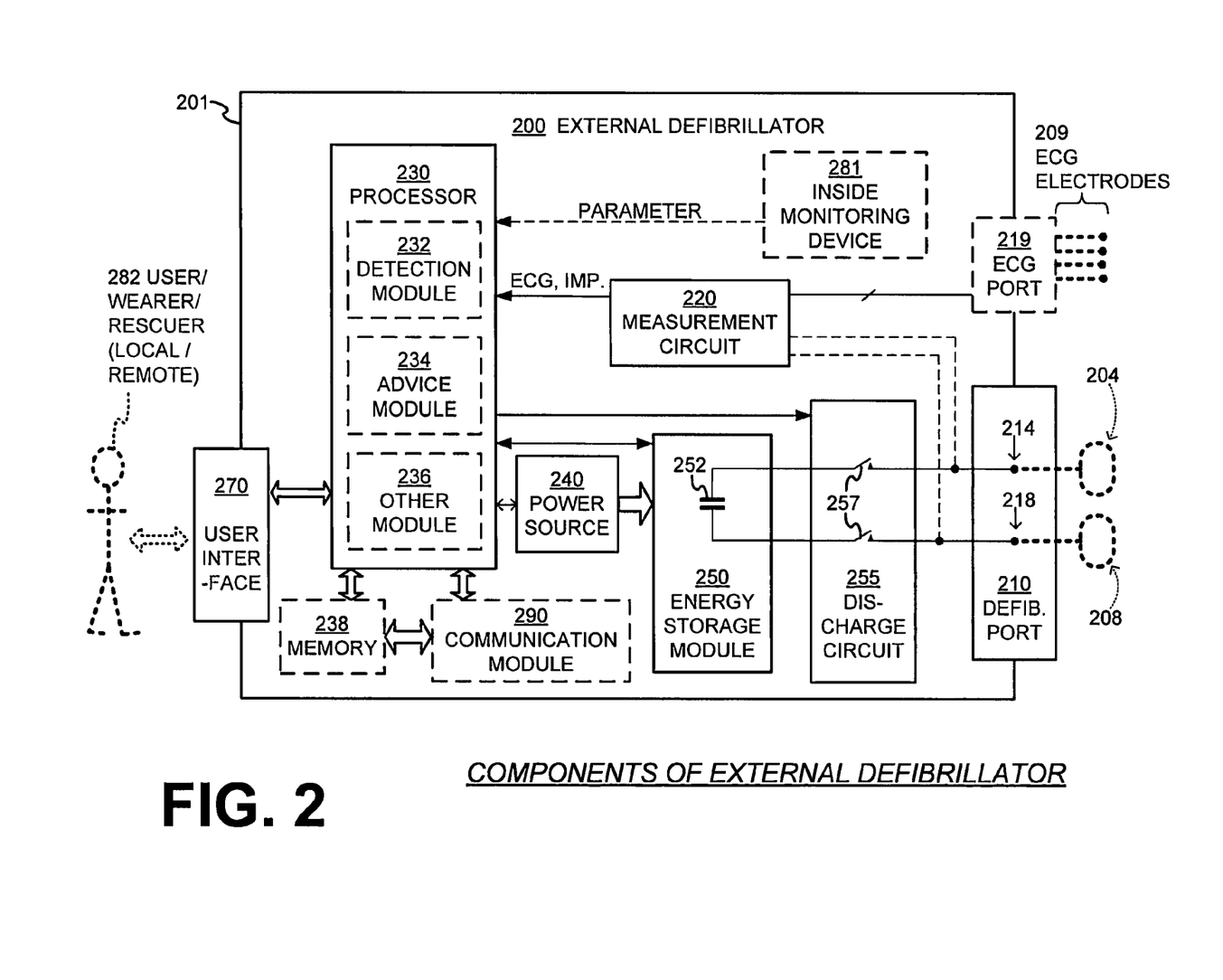
FIG. 2 is a diagram showing components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as person 82 of FIG. 1. Defibrillator 200 may further include a user interface 270 for a user 282. User 282 can be patient 82, also known as wearer 82, if conscious. Or user 282 can be a local rescuer at the scene, such as a bystander who might offer assistance, or a trained person. Or, user 282 might be a remotely located trained caregiver in communication with the wearable defibrillator system.

Defibrillator 200 may include an internal monitoring device 281. Device 281 is called an "internal" device because it is incorporated within housing 201. Monitoring device 281 can monitor patient parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations.

Patient physiological parameters include, for example, those physiological parameters that can be of any help in detecting by the wearable defibrillation system whether the patient is in need of a shock, plus optionally their history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and maybe sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Monitoring device 180 or monitoring device 281 may include a motion detector, which can be made in many ways as is known in the art. Or, one of these monitoring devices could include a location sensor such as a Global Positioning System (GPS), which informs of the location, and the rate of change of location over time. Many motion detectors output a motion signal that is indicative of the motion of the detector, and thus of the patient's body. Patient state parameters can be very helpful in narrowing down the determination of whether SCA is indeed taking place.

System parameters of a wearable defibrillation system can include system identification, battery status, system date and time, reports of self-testing, records of data entered, records of episodes and intervention, and so on.

Environmental parameters can include ambient temperature and pressure. A humidity sensor may provide information as to whether it is raining. Presumed patient location could also be considered an environmental parameter. The patient location could be presumed if monitoring device 180 or 281 includes a GPS sensor.

Defibrillator 200 typically includes a defibrillation port 210, such as a socket in housing 201. Defibrillation port 210 includes nodes 214, 218. Defibrillation electrodes 204, 208, for example similar to electrodes 104, 108 of FIG. 1, can be plugged into defibrillation port 210. Plugging can be from their leads, such as leads 105 of FIG. 1, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge delivered to the wearer will be the shock for defibrillation, pacing, and so on.

Defibrillator 200 may optionally also have an ECG port 219 in housing 201, for plugging in ECG electrodes 209, which are also known as ECG leads. It is also possible that ECG electrodes 209 can be connected continuously to ECG port 219, instead. EGG electrodes 209 can help sense an ECG signal, e.g. a 12-lead signal, or a signal from a different number of leads, especially if they make good electrical contact with the body of the patient. ECG electrodes 209 can be attached to the inside of support structure 170 for making good electrical contact with the patient, similarly as defibrillation electrodes 204, 208.

Defibrillator 200 also includes a measurement circuit 220. Measurement circuit 220 receives physiological signals from EGG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or ECG electrodes 209 are not making good electrical contact with the patient's body. These physiological signals can be sensed, and information about them can be rendered by circuit 220 as data, other signals, etc.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232. Detection module 232 can include a ventricular fibrillation ("VF") detector. The patient's sensed ECG from measurement circuit 220 can be used by the VF detector to determine whether the patient is experiencing VF. Detecting VF is useful, because VF results in SCA.

Another such module in processor 230 can be an advice module 234, which generates advice for what to do. The advice can be based on outputs of detection module 232. There can be many types of advice according to embodiments. As one example, a Shock Advisory Algorithm can render the advice to shock the patient by delivering a charge, as opposed to not shock the patient. Shocking can be for defibrillation, pacing, and so on.

Processor 230 can include additional modules, such as other module 236, for other functions. In addition, if monitoring device 281 is indeed provided, it may be operated in part by processor 230, etc.

In some embodiments, processor 230 is configured to determine whether the patient who is wearing the wearable defibrillation system meets an unconscious bradyarrhythmia condition. The unconscious bradyarrhythmia condition can be defined in a number of ways according to embodiments. One such way is if the patient's heart rate is less than a threshold, such as 45 beats per minute (bpm), 40 bpm, 35 bpm or even less. At such low heart rates, people are known to become unconscious. As such, the unconscious bradyarrhythmia condition is a proxy for inferring when the patient is unconscious. The determination about the unconscious bradyarrhythmia condition being met can further be confirmed, as will be seen later in this document.

The unconscious bradyarrhythmia condition is detected because, while most sudden cardiac arrests are caused by a ventricular tachyarrhythmia, it is possible for a cardiac arrest to be caused by extreme bradyarrhythmia (asystole or extreme bradycardia). While a high-energy shock can be effective for treating a ventricular tachyarrhythmia. It can be useless for treating an extreme bradyarrhythmia. When a patient has such bradyarrhythmia, he could also faint, i.e. become unconscious.

There are a number of ways for determining whether the unconscious bradyarrhythmia condition is met. In some embodiments, the determination is made from the physiological parameter, either in part or exclusively. In other embodiments, the determination is made from the patient's ECG, such as by counting QRS complexes.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory-devices, any combination of these, and so on. Memory 238 is thus a non-transitory storage medium. Memory 238, if provided, can include programs for processor 230, and so on. The programs can include sets of instructions. The programs can be operational for the inherent needs of processor 230, and can also include protocols and ways that decisions can be made by advice module 234. In addition, memory 238 can store prompts for user 282, if they are a local rescuer. Moreover, memory 238 can store data. The data can include patient data, system data and environmental data, for example as learned by monitoring device 281 and monitoring device 180. The data can be stored memory 235 before it is transmitted out of defibrillator 200, or stored there after it is received by it.

Defibrillator 200 may also include a power source 240. To enable portability of defibrillator 200, power source 240 typically includes a battery. Such a battery is typically implemented as a battery pack, which can be rechargeable or not. Sometimes, a combination is used, of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support, structure of the wearable system. Module 250 is where some electrical energy is stored, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of electrical charge, for delivering to the patient.

Defibrillator 200 moreover includes a discharge circuit 255. Circuit 255 can be controlled to permit the energy stored in module 250 to be discharged to nodes 214, 218, and thus also to defibrillation electrodes 204, 208. Circuit 255 can include one or more switches 257. Those can be made in a number of ways, such as by an H-bridge, and so on.

In embodiments, if it is determined that the patient meets the unconscious bradyarrhythmia condition, portions of the stored electrical charge are delivered to the patient as pacing pulses or shocks. Such pulses are seen in FIG. 1 as pulse 111, except that pacing pulses do not have the high energy of defibrillation pulses.

User interface 270 can be made in any number of ways. User interface 270 may include output devices, which can be visual, audible or tactile, for communicating to a user. User interface 270 may also include input devices for receiving inputs from users. For example, interface 270 may include a screen, to display what is detected and measured, provide visual feedback to rescuer 282 for their resuscitation attempts, and so on. Interface 270 may also include a speaker, to issue voice prompts, etc. Sounds, images, vibrations, and anything that can be perceived by user 282 can also be called human perceptible indications. Interface 270 may additionally include various controls, such as pushbuttons, keyboards, touchscreens, a microphone, and so on. In addition, discharge circuit 255 can be controlled by processor 230, or directly by user 282 via user interface 270, and so on.

In some embodiments, an output device of user interface 270 is configured to issue a query to the patient, after the unconscious bradyarrhythmia condition is determined to be met, as a warning. The query can be spoken, or tactile, and intended for the patient to reply so as to confirm that he is fine. An input device of user interface 270 can be configured to receive an input from the patient in response to the query, for example within a preset available-reply time. In such embodiments, the unconscious bradyarrhythmia condition can be confirmed to be met if the input device does not receive the input, such as within the specific reply time.

In addition, an output device of user interface 270 can be configured to transmit a warning to bystanders, if the patient is determined to meet the unconscious bradyarrhythmia condition. The warning could include an appraisal of the situation, and possibly include a request to call for help.

Defibrillator 200 can optionally include a communication module 290, for establishing one or more wired or wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, episode information, therapy attempted, CPR performance, system data, environmental data, and so on.

In some embodiments, communication module 290 is configured to transmit an alert message to a remotely located third party, if the patient is determined to meet the unconscious bradyarrhythmia condition. This way, the third party can send for help.

Defibrillator 200 can optionally include other components.

Some patients with extreme bradyarrhythmia respond to transthoracic pacing, in which a pacing stimulus triggers ventricular depolarization, in which the left ventricle contracts and ejects a bolus of blood into the aorta. For example, transthoracic pacing is commonly used when a patient develops third degree atrioventricular block, which can happen during an acute myocardial infarction. In such cases, the pacing is continued until either the atrioventricular block goes away, or help arrives for the patient, such as the patient being admitted at an electrophysiology laboratory to have a long-term pacemaker implanted. Particular patterns of pacing are now described.

Figure 3A:
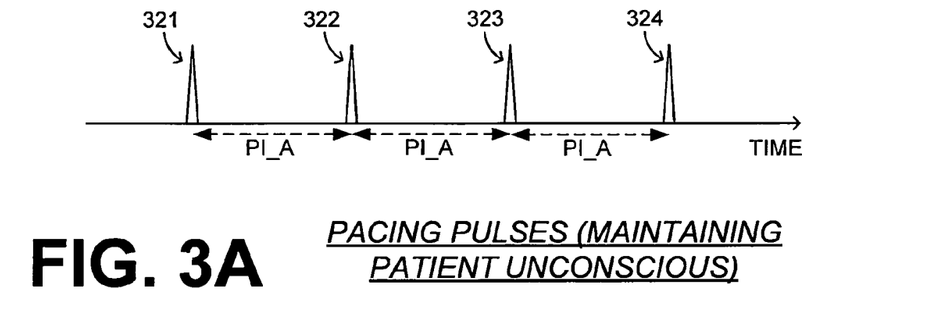
FIG. 3A is a timing diagram of pacing pulses delivered according to embodiments.

FIG. 3A is a timing diagram of pacing pulses delivered according to embodiments. Pacing pulses 321, 322, 323, 324 are shown as monophasic, but they equivalently could be biphasic. Pacing pulses 321, 322, 323, 324 are delivered at a uniform pacing interval PI_A, the inverse of which defines a pacing frequency or rate.

Optionally, the pacing frequency is purposely slower than a person's normal heartbeat frequency, so that the patient will not regain consciousness. For example, the pacing frequency can be less than 50 beats per minute (bpm) or 45 bpm, or even a lesser frequency. As such, the patient can be paced for a long time without the discomfort of experiencing the pacing pulses while conscious. It will be appreciated that such a pacing frequency is often still faster than the patient's original bradyarrhythmia pulse, and thus the intervention of pacing is much more likely to preserve the patient's blood flow, and prevent damage to the patient's organs.

In some embodiments, pacing-on-demand is implemented. For example, processor 230 can be configured to detect perfusion pulses occurring naturally in the patient. Detection can be performed in many ways, such as for example using the same instrumentality that was used to determine that the unconscious bradyarrhythmia condition was met, or one of the monitoring devices. In such embodiments, after the last detected naturally occurring perfusion pulse, a subsequent pacing pulse is then delivered. The subsequent pacing pulse can be delivered at least after a pacing interval has elapsed, which corresponds to a frequency of 50 bpm, 45 bpm, 40 bpm, 35 bpm or less. An example is now described.

Figure 3B:
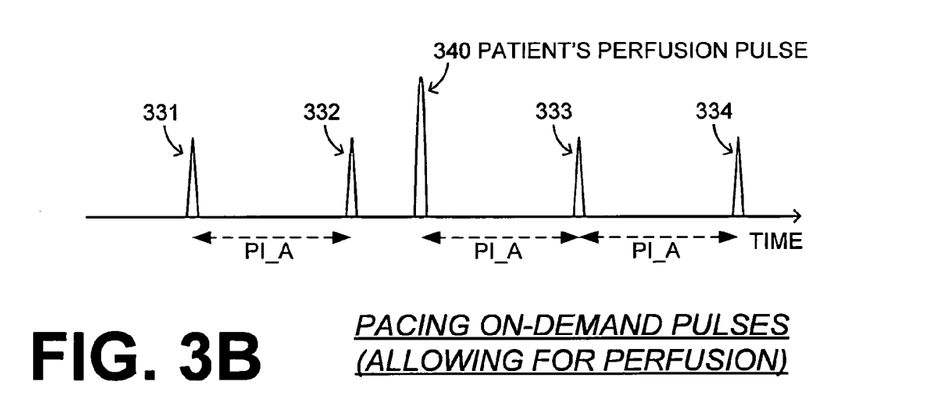
FIG. 3B is a timing diagram of pacing pulses delivered according to embodiments, in which a perfusion pulse occurring naturally in the patient has been detected.

FIG. 3B is a timing diagram of pacing pulses delivered according to embodiments. Pacing pulses 331, 332, 333, 334 were initially intended to be delivered at pacing interval PI_A, similar to that of FIG. 3A. However, a patient's perfusion pulse 340 is detected. Accordingly, after pulse 340 subsequent pulse 333 is delivered later, e.g. after pacing interval PI_A.

A system according to embodiments may face a tradeoff in competing desires. One desire is for the pacing frequency to be high, so as to pump as much blood as possible to the organs. The competing desire is for the pacing frequency to not be so high as to help the patient regain consciousness, for the time being. An optimum pacing frequency can thus be defined for the patient. The challenge is that each patient may have a different such optimum frequency. The sample values mentioned above are drawn from the experience that generally people at these heart rates do not stay conscious.

According to embodiments, the pacing frequency can thus be changed. The sample values mentioned above can be used as a first frequency, in which the pacing pulses can initially be delivered. However, if it is later determined that the patient no longer meets the unconscious bradyarrhythmia condition, the pacing pulses are then delivered at a second frequency that is smaller than the first frequency. An example is now described.

Figure 3C:
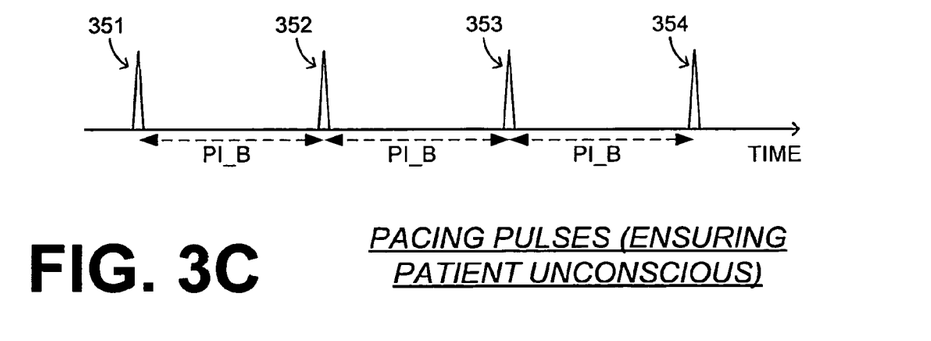
FIG. 3C is a timing diagram of pacing pulses delivered according to embodiments, in which the pacing interval has been elongated from that of FIG. 3A so as to ensure the patient will not regain consciousness at this time.

FIG. 3C is a timing diagram of pacing pulses delivered according to embodiments. Pacing pulses 351, 352, 353, 354 are delivered at a pacing interval PI_B, which is elongated from PI_A of FIG. 3A, so as to ensure the patient will not regain consciousness at this time. Given the inverse relationship, the longer pacing interval PI_B corresponds to a lesser pacing frequency than the pacing frequency of FIG. 3A.

Even if the initial pacing frequency does not help the patient to regain consciousness, a system might not know if the patient can be paced at a higher frequency still without regaining consciousness. So, in some embodiments, while the pacing pulses are initially delivered at a first frequency, the pacing pulses can then be delivered at a second frequency that is larger than the first frequency. However, if it is later determined that the patient no longer meets the unconscious bradyarrhythmia condition, the pacing pulses can then be delivered at a third frequency that is smaller than the second frequency. In some embodiments, the third frequency is the same as the first frequency.

The above-mentioned devices and/or systems perform functions, processes and/or methods, as described in this document. The functions, processes and/or methods may be implemented by one or more devices that include logic circuitry. The logic circuitry may include a processor that may be programmable for a general purpose, or dedicated, such as processor 230.

The logic circuitry may also include one or more storage media, such as memory 238 or another memory. Such a storage medium can be a non-transitory computer-readable medium. These storage media, individually or in combination with others, can have stored thereon programs that the processor may be able to read, and execute. More particularly, the programs can include instructions in the form of code, which the processor may be able to execute upon reading. Executing is performed by physical manipulations of physical quantities, and may result in the functions, processes and/or methods to be performed. In addition, these storage media may store data.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalents aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 4:
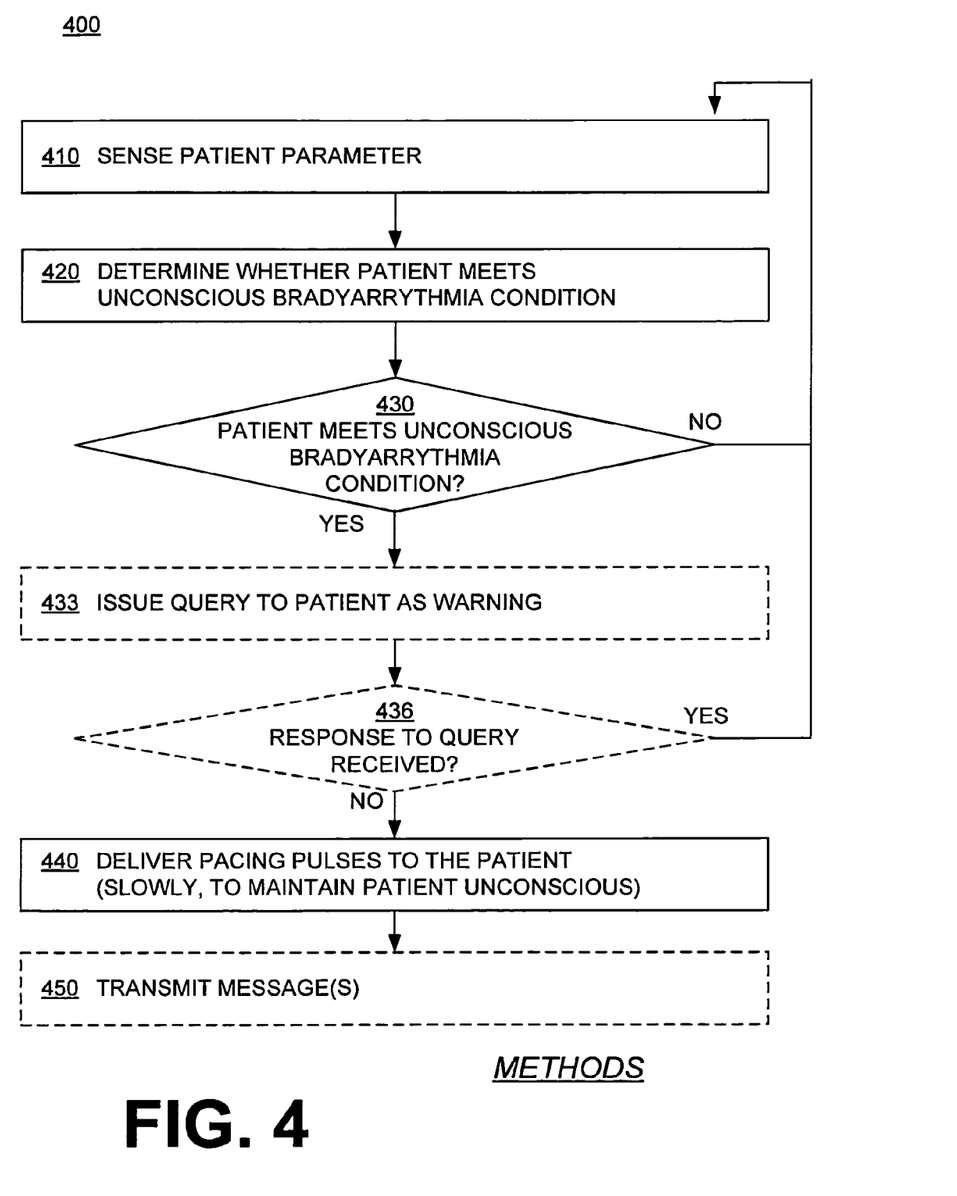
FIG. 4 is a flowchart for illustrating methods according to embodiments.

FIG. 4 shows a flowchart 400 for describing methods according to embodiments. The methods of flowchart 400 may also be practiced by embodiments described above.

According to an operation 410, a patient parameter is sensed. The parameter can be the patient's ECG, or a physiological parameter other than the ECG, such as from one of the monitoring devices.

According to another operation 420, it is determined whether the patient meets an unconscious bradyarrhythmia condition. Operation 420 can be done and confirmed as described above.

According to another, optional operation 430, if the patient is not determined to meet the unconscious bradyarrhythmia condition, execution can return to operation 410. Else, according to another optional operation 433, a query can be issued to the patient as a warning. Then according to another operation 436, if a response to the query is received; execution can return to operation 430. Else, according to another operation 440, pacing pulses are delivered to the patient. The pulses can be at pacing frequencies as described elsewhere in this document.

According to a further, optional operation 450, messages can be transmitted. A message can be a warning to bystanders and/or an alert message to a remotely located third party, as per the above.

Figure 5:
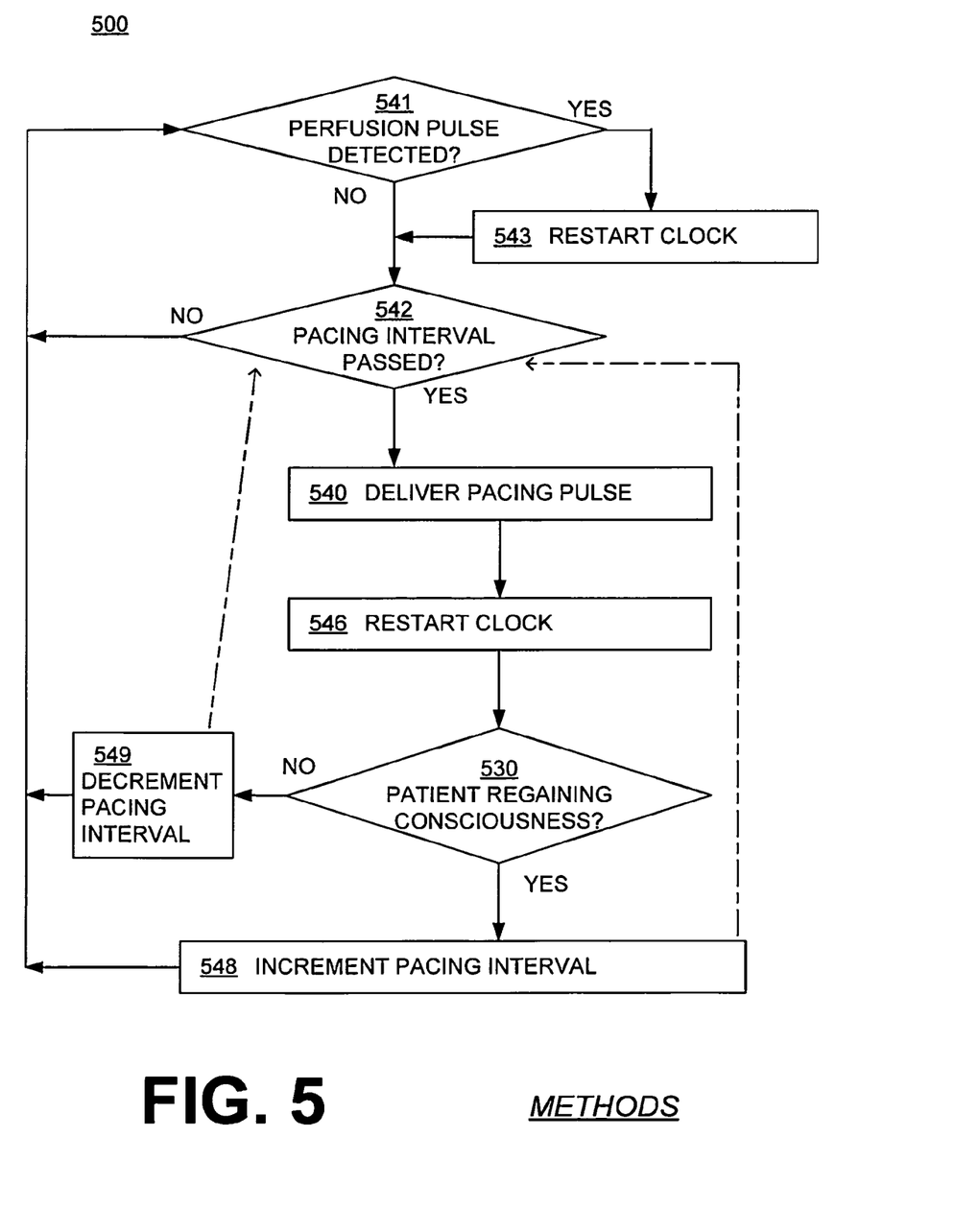
FIG. 5 is a flowchart for illustrating methods according to embodiments.

FIG. 5 shows a flowchart 500 for describing methods according to embodiments, for particularly managing the timing and frequency of pacing pulses. The methods of flowchart 500 may also be practiced by embodiments described above.

According to an operation 541, it is inquired whether a perfusion pulse is detected. If not, then according to another, optional operation 542, it is inquired whether a pacing interval has passed. If not, the execution returns to operation 541. If, however, at operation 541 a perfusion pulse is detected, such as pulse 340 in FIG. 3B, then according to another, optional operation 543, a clock is restarted for the pacing interval. Execution then returns to operation 542. The restarting can accommodate on-demand pacing, such as for pulse 333 waiting for a full pacing interval after pulse 340 in FIG. 3B.

At operation 542, when the pacing interval has indeed passed, according to another operation 540, a pacing pulse is delivered. Then according to another operation 546, the clock for the pacing pulse is restarted, similarly with operation 543.

Then, according to another, optional operation 530, it is inquired whether the patient is regaining consciousness. Operation 530 can be implemented in any number of ways, such as by exploiting a patient parameter, the output of a motion detector, and so on. If yes, then according to another, optional operation 548, the pacing interval is incremented, so as to reduce the pacing frequency. If not, then according to another, optional operation 549, the pacing interval may be decremented, so as to increase the pacing frequency. Operations 548 and 549 will impact operation 542, which is a relationship indicated with dot-dash arrows.

Optional operations 530, 548 and 549 are intended for searching and finding the optimum pacing frequency of the patient for the criteria described above. Once that frequency is found, then operations 530, 548 and 549 may be skipped from flowchart 500. A method is now described in more detail.

The optimum pacing frequency may be found heuristically, according to embodiments where the pacing frequency is changed until the optimum is found. An example is now described.

Figure 6:
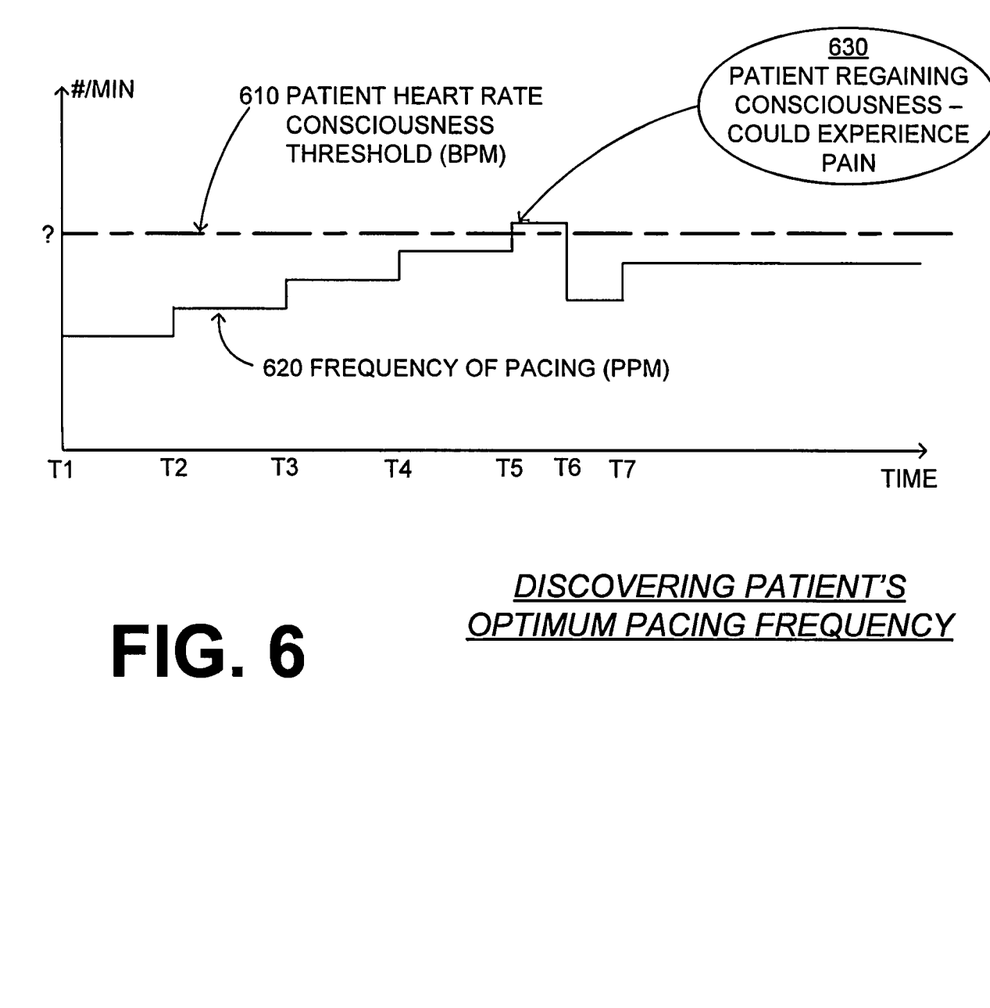
FIG. 6 is a diagram showing how an optimum pacing frequency may be found heuristically according to embodiments.

FIG. 6 is a diagram showing how an optimum pacing frequency may be found heuristically according to embodiments. The procedure of FIG. 6 may be performed by the wearable defibrillator system during an actual episode, or in a doctor's office when a patient is first fitted with the wearable defibrillator system.

In FIG. 6, the horizontal axis is for time, and the vertical axis is for a number of occurrences per minute. Line 610 defines the heart rate consciousness threshold of the patient, in bpm. If the patient's heart is beating faster, he would be conscious, while if slower, unconscious. Line 610 could be a zone, and so on. By the time it is determined that the patient meets the unconscious bradyarrhythmia condition, his heart rate can be below line 610, and the patient is unconscious. Importantly, that threshold is not known for every patient, which is why line 610 intercepts the vertical axis at a value shown with a question mark.

Broken line 620 indicates the actual frequency of pacing, in pulses per minute ("PPM"). A time T1, line 620 starts at a certain value. Then, thanks to operation 549 of FIG. 5, line 620 is incremented at times T2, T3, T4, T5, in search of line 610. Incrementing can be dynamic, automatically, or by the doctor. Incrementing should have hysteresis, to avoid going back and forth with small changes in pacing rate. The hysteresis may be implemented by not switching up very quickly. At time T5, according to comment 630, it is detected that the patient is regaining consciousness. At that time, line 610 has been identified as some value that was crossed at time T5. Then the final pacing frequency can be determined at a level close to, but less than line 610, and applied, such as after time T7. Optionally, before T7, at time T6 the pacing frequency is dropped sharply for a little time, to ensure the patient becomes unconscious again, and then at T7 it is raised again at the level closer to, but less than line 610.

The invention can also be applied to external defibrillators, based on the present description. External defibrillators used by hospitals end EMS teams can detect bradyarrhythmia, and provide pacing pulses. When it comes to dealing with discomfort, they typically have the means of sedating the patient while keeping him conscious.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced, indeed, examples or embodiments of the invention may be practiced according to what is described, or yet differently, and also in conjunction with other present or future technologies.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, white providing the advantages of the features incorporated in such combinations and sub-combinations.

The following claims define certain combinations and sub-combinations of elements, features and steps or operations, which are regarded as novel and non-obvious. Additional claims for other such combinations and subcombinations may be presented in this or a related document.

What is claimed is:

1. A wearable defibrillation system comprising:
a support structure configured to be worn by a patient;
a charge storage module coupled to the support structure and configured to store charge;
electrodes configured to detect an ECG of the patient;
a monitoring device other than the electrodes configured to sense a physiological parameter of the patient other than the ECG; and
a processor configured to determine at least in part from the physiological parameter whether the patient meets an unconscious bradyarrhythmia condition, and
in which portions of the charge are delivered to the patient as pacing pulses if it is determined that the patient meets the unconscious bradyarrhythmia condition.

2. The system of claim 1, in which
the monitoring device includes one of a perfusion sensor, a pulse oximeter, a Doppler device for detecting blood flow, a cuff for detecting blood pressure, an optical sensor, an illumination detector, a source for detecting color change in tissue, a motion sensor, a device that can detect artery wall movement, a device that can detect heart wall movement, a sound sensor, a device with a microphone, and an SpO2 sensor.

3. The system of claim 1, in which
the unconscious bradyarrhythmia condition is determined to be met if the physiological parameter indicates that the patient's heart rate is less than 45 bpm.

4. The system of claim 1, further comprising:
an output device configured to issue a query to the patient; and
an input device configured to receive an input in response to the query, and
in which the unconscious bradyarrhythmia condition is confirmed to be met if the input device does not receive the input.

5. The system of claim 1, further comprising:
an output device configured to transmit a warning to bystanders if the patient is determined to meet the unconscious bradyarrhythmia condition.

6. The system of claim 1, further comprising:
a communication module configured to transmit an alert message to a remotely located third party if the patient is determined to meet the unconscious bradyarrhythmia condition.

7. The system of claim 1, in which
at least two successive pacing pulses occur at a pacing interval that corresponds to a frequency a less than 50 bpm.

8. The system of claim 1, in which
the processor is configured to detect perfusion pulses occurring naturally in the patient, and
after the last detected naturally occurring perfusion pulse, a subsequent pacing pulse is delivered at least after a pacing interval that corresponds to a frequency of 50 bpm has elapsed.

9. The system of claim 1, in which
the pacing pulses are initially delivered at a first frequency, and
if it is later determined that the patient no longer meets the unconscious bradyarrhythmia condition, the pacing pulses are then delivered at a second frequency that is smaller than the first frequency.

10. The system of claim 1, in which
the pacing pulses are initially delivered at a first frequency, the pacing pulses are then delivered at a second frequency that is larger than the first frequency, but
if it is later determined that the patient no longer meets the unconscious bradyarrhythmia condition, the pacing pulses are then delivered at a third frequency that is smaller than the second frequency.

11. A wearable defibrillation system comprising:
a support structure configured to be worn by a patient;
a charge storage module coupled to the support structure and configured to store charge;
electrodes configured to sense an ECG of the patient; and
a processor configured to determine at least in part from the ECG whether the patient meets an unconscious bradyarrhythmia condition, and
in which portions of the charge are delivered to the patient as pacing pulses if it is determined that the patient meets the unconscious bradyarrythmia condition, the pacing pulses being delivered at a frequency of less than 45 bpm.

12. The system of claim 11, in which
the unconscious bradyarrhythmia condition is determined to be met if the ECG indicates that the patient's heart rate is less than 45 bpm.

13. The system of claim 11, further comprising:
an output device configured to issue a query to the patient; and
an input device configured to receive an input in response to the query, and in which the unconscious bradyarrhythmia condition is confirmed to be met if the input device does not receive the input.

14. The system of claim 11, further comprising:
an output device configured to transmit a warning to bystanders if the patient is determined to meet the unconscious bradyarrhythmia condition.

15. The system of claim 11, further comprising:
a communication module configured to transmit an alert message to a remotely located third party if the patient is determined to meet the unconscious bradyarrhythmia condition.

16. The system of claim 11, in which
the processor is configured to detect perfusion pulses occurring naturally in the patient, and
after the last detected naturally occurring perfusion pulse, a subsequent pacing pulse is delivered at least after a pacing interval that corresponds to a frequency of 45 bpm has elapsed.

17. The system of claim 11, in which
if it is later determined that the patient no longer meets the unconscious bradyarrhythmia condition, the pacing pulses are then delivered at a subsequent frequency that is smaller than 45 bpm.

18. The system of claim 11, in which
the pacing pulses are then delivered at a second frequency that is larger than 45 bpm, but
if it is later determined that the patient no longer meets the unconscious bradyarrhythmia condition, the pacing pulses are then delivered at a third frequency that is smaller than the second frequency.

19. A non-transitory computer-readable storage medium storing one or more programs which, when executed by a wearable defibrillation system worn by a patient, they result in:
causing to be sensed a physiological parameter of the patient other than the patient's ECG;
causing to be determined at least in part from the physiological parameter whether the patient meets an unconscious bradyarrhythmia condition; and
if so, causing to be delivered pacing pulses to the patient.

20. A non-transitory computer-readable storage medium storing one or more programs which, when executed by a wearable defibrillation system worn by a patient, they result in:
causing the patient's ECG to be sensed;
causing to be determined at least in part from the ECG whether the patient meets an unconscious bradyarrhythmia condition; and
if so, causing pacing pulses to be delivered to the patient at a frequency of less than 45 bpm.

21. A method for a wearable defibrillation system worn by a patient, comprising:
sensing is physiological parameter of the patient other than the patient's ECG;
determining at least in part from the physiological parameter whether the patient meets an unconscious bradyarrhythmia condition; and
if so, delivering pacing pulses to the patient.

22. The method of claim 21, in which
the unconscious bradyarrhythmia condition is determined to be met if the physiological parameter indicates that the patients heart rate is less than 40 bpm.

23. The method of claim 21, further comprising:
issuing a query to the patient;
then waiting for an input in response to the query, and
in which the unconscious bradyarrhythmia condition is determined to be met if no input is received.

24. The method of claim 21, further comprising:
transmitting a warning to bystanders if the patient is determined to meet the unconscious bradyarrhythmia condition.

25. The method of claim 21, further comprising:
transmitting an alert message to a remotely located third party if the patient is determined to meet the unconscious bradyarrhythmia condition.

26. The method of claim 21, in which
at least two successive pacing pulses occur at a pacing interval that corresponds to a frequency of less than 50 bpm.

27. The method of claim 21, further comprising:
detecting perfusion pulses occurring naturally in the patient, and
after the last detected naturally occurring perfusion pulse, a subsequent pacing pulse is delivered at least after a pacing interval that corresponds to a frequency of 50 bpm has elapsed.

28. The method of claim 21, in which
the pacing pulses are initially delivered at a first frequency, and
if it is later determined that the patient no longer meets the unconscious bradyarrhythmia condition, the pacing pulses are then delivered at a second frequency that is smaller than the first frequency.

29. The method of claim 21, in which
the pacing pulses are initially delivered at a first frequency,
the pacing pulses are then delivered at a second frequency that is larger than the first frequency, but
if it is later determined that the patient no longer meets the unconscious bradyarrhythmia condition, the pacing pulses are then delivered at a third frequency that is smaller than the second frequency.

30. A method for a wearable defibrillation system worn by a patient, comprising:
sensing the patient's ECG;
determining at least in part from the ECG whether the patient meets an unconscious bradyarrhythmia condition; and
if so, delivering pacing pulses to the patient at a frequency of less than 45 bpm.

* * * * *